United States Patent [19]
MacMillan et al.

[11] Patent Number: 6,156,082
[45] Date of Patent: Dec. 5, 2000

[54] FUEL ADDITIVES

[75] Inventors: John A MacMillan; Mark L. Brewer, both of South Wirral, United Kingdom

[73] Assignee: The Associated Octel Company Limited, London, United Kingdom

[21] Appl. No.: 09/194,357

[22] PCT Filed: May 30, 1997

[86] PCT No.: PCT/GB97/01469

§ 371 Date: Dec. 28, 1998

§ 102(e) Date: Dec. 28, 1998

[87] PCT Pub. No.: WO97/45507

PCT Pub. Date: Dec. 4, 1997

[30] Foreign Application Priority Data

May 31, 1996 [GB] United Kingdom .................... 9611406
Sep. 20, 1996 [GB] United Kingdom .................... 9619701

[51] Int. Cl.[7] ........................................................ C10L 1/18
[52] U.S. Cl. .................................................................. 44/398
[58] Field of Search ................................ 44/398; 560/190, 560/193, 198, 200

[56] References Cited

U.S. PATENT DOCUMENTS

| | | |
|---|---|---|
| 2,993,773 | 7/1961 | Stromberg . |
| 3,273,981 | 9/1966 | Furey . |
| 3,287,273 | 11/1966 | Furey et al. . |
| 3,871,837 | 3/1975 | Bedague et al. . |
| 4,129,508 | 12/1978 | Friihauf . |
| 4,216,114 | 8/1980 | Baker . |
| 4,448,586 | 5/1984 | Weidig . |
| 4,728,340 | 3/1988 | Vos . |
| 4,874,395 | 10/1989 | Meyer . |
| 5,080,817 | 1/1992 | Meyer . |

FOREIGN PATENT DOCUMENTS

| | | |
|---|---|---|
| 0 235 868 | 9/1987 | European Pat. Off. . |
| 2 169 718 | 9/1973 | France . |
| 20 29 804 | 12/1970 | Germany . |
| 896 376 | 5/1962 | United Kingdom . |
| 981 850 | 1/1965 | United Kingdom . |
| 1 055 337 | 1/1967 | United Kingdom . |
| 94 17160 | 4/1994 | WIPO . |

*Primary Examiner*—Jerry D. Johnson
*Attorney, Agent, or Firm*—Nixon & Vanderhye

[57] ABSTRACT

Compounds of formula (I)

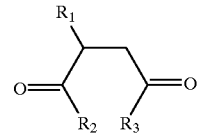

where $R_1$ is a $C_{10}$–$C_{32}$ alkenyl group and $R_2$ and $R_3$ are $-(-OCH_2CH_2-)_nOH$, $-(-OCH_2CHCH_3-)_nOH$ or $-OCH_2CHOHCH_2OH$ in which n is an integer from 1 to 10 are lubricity and corrosion-prevention additives for fuels.

5 Claims, No Drawings

FUEL ADDITIVES

This invention relates to fuel additives, more particularly to additives which increase the lubricity of the fuel and avoid undesirable interactions with the other additives now commonly present in fuels. The additives have also been found to possess surprisingly useful anti-corrosion properties.

It is known to add a minor proportion of a long chain fatty acid to liquid hydrocarbon fuels to increase the lubricity of the fuel, that is the ability to prevent wear on contacting metal surfaces. Increased lubricity results in lower wear to the surface, as measured for example by the well known wear scar test described in more detail hereinafter. Fatty acids which have been used for this purpose include di-linoleic acid. However, the increasing number of additives now present in fuels, and increased dosing levels, means that a need is arising for lubricity additives with an inherently lower tendency to interact with other fuel and lubricant additives. Improved lubricity performance for such compounds, relative to known lubricity additives, would also be desirable.

Esters of fatty acids have also been proposed as lubricity additives. Whilst the acid functions of these molecules are blocked by an alkyl ester group and so are not available for interaction with other fuel additives, it is important that the performance of the lubricity additive is not reduced by esterification, so that a delicate balance of properties is required.

U.S. Pat. No. 4,448,586 (to Weidig) discloses liquid fuels having anti-corrosion properties for use in internal combustion engines. The corrosion inhibition is discussed in relation to alkanol-type fuels and the reactant ratios are such that $RCOO.CH_2CH_2.OOCR$ structures are present.

U.S. Pat. No. 4,874,395 (to Meyer) also discloses corrosion inhibitor compositions for hydrocarbon fuels comprising a $C_{10}$–$C_{24}$ alkenyl succinimide anhydride partially esterified with a water-soluble glycol. However, the ester is then neutralised with an amine in order to neutralise residual acid groups. Such acid groups are not present in the compounds of the present invention.

FR-A-2169718 (to Institut Français du Pétrole, des Carburants et Lubrifiants) discloses lubricating oils comprising 10 to 100% of esters, polyesters or esters of ethers of polyalkyleneglycols represented by the formula HO(R—O)$_n$H wherein each R is a divalent aliphatic $C_2$–$C_5$ radical and n=2–50.

GB-A-1055337 (to Lubrizol) discloses oil-soluble esters of a substantially hydrocarbon-substituted succinic acid wherein the substantially saturated hydrocarbon substituent has at least 50 aliphatic carbon atoms.

GB-A-1306233 (to Lubrizol) discloses a fuel composition comprising a major amount of a petroleum and a minor amount of a dispersant composition comprising at least one oil-soluble carboxylic dispersant including a substantially saturated hydrocarbon-substituted carboxylic group having at least 30 aliphatic carbon atoms in the hydrocarbon substituent and a stock petroleum fraction, the weight ratio of petroleum fraction to carboxylic dispersant being from 20:1 to 1:10.

We have now discovered a class of esterified alkenyl succinic acids which, while demonstrating excellent performance as lubricity additives, also offer improved compatibilities with other fuel and lubricant additives.

The novel compounds are represented by the general formula (I)

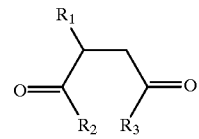

where $R_1$ is a $C_{10}$–$C_{32}$ alkenyl group, such as an olefin or polyolefin, $R_2$ and $R_3$ are —(OCH$_2$CH$_2$)$_n$OH, —(OCH$_2$CHCH$_3$)$_n$OH or —OCH$_2$CHOHCH$_2$OH with n=1–10.

$R_1$ is most preferably a $C_{12}$–$C_{26}$ group. The value of n is preferably 1 or 2.

The compounds of formula (I) may be added to middle distillate fuels of poor lubricity, such as those with poor inherent lubricity, and those which have been exposed to hydrotreatment or desulphurisation processes thereby lowering the sulphur concentration to 0.5% w/w or less, for example diesel fuels (typical distillation range 150–400° C.) and heating oils (typical distillation range 150–450° C.), and also to gasolines (typical distillation range 30–210° C.), kerosines (typical distillation range 140–300° C.) and heavy fuel oils (typical distillation range 300–600° C.). A further aspect of the invention thus comprises methods of increasing the lubricity of such fuels by addition of the compounds of the invention.

Compounds of formula (I) may be dosed in amounts between 5 and 5000 ppm, preferably between 10 and 500 ppm and most preferably between 30 and 300 ppm, to improve the lubricity properties of the fuels.

Diesel fuels and heating oils will typically contain less than 0.2% w/w sulphur and may contain, in addition to the additive compositions of this invention, any of the other additives commonly added as minor components, such as cetane improvers, cold flow improvers, detergent/dispersant additives, antifoam additives, dehazing additives, combustion improvers, antioxidants, etc.

As used herein, "gasoline" refers to motor fuels meeting ASTM standard D-439, and includes blends of distillate hydrocarbon fuels with oxygenated components, such as MTBE, ETBE, ethanol, etc. as well as the distillate fuels themselves. The fuels may be leaded or unleaded, and may contain, in addition to the additive compositions of this invention, any of the other additives conventionally added to gasolines, such as scavengers, anti-icing additives, octane requirement improvers, detergent packages, antioxidants, demulsifiers, corrosion inhibitors, etc.

The compounds of formula (I) have also been found to possess surprisingly useful anti-corrosion properties. Thus in certain oil refinery and pipeline cargo applications a corrosion inhibitor is required which will be resistant to base neutralisation. The base, typically sodium hydroxide, can be present in fuels which have undergone a refinery sweetening treatment. The consequence of base neutralisation is deactivation of added corrosion inhibitors and consequent levels of rust which are typical of a fuel without added corrosion inhibitors.

The compounds of formula (I), however, have been found to provide effective corrosion inhibition which is resistant to base deactivation. Thus a further aspect of the invention provides a method of inhibiting corrosion on a metal surface exposed to a liquid hydrocarbon fuel, comprising the addition to said fuel of a compound of formula (I) as defined above. The metal surface, typically a pipeline or other metal vessel as used in fuel transport and/or in known refinery processes, will generally be of iron or steel.

Compounds of formula I may be added in amounts between 5 and 5000 ppm, preferably between 10 and 500 ppm and most preferably between 30 and 300 ppm, to achieve the desired corrosion inhibition in the fuel.

The invention also provides fuel additive compositions suitable for use in any of the previous aspects of the invention, the compositions comprising one or more compounds of formula (I) in a fuel-miscible solvent, for example toluene, xylene or Shellsol (available from Shell), and optionally other ingredients conventionally used in fuel additive packages.

The compounds of formula (I) may for example be prepared by reacting an anhydride of formula

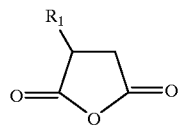

with an alcohol of formula $R_2OH$ and/or $R_3OH$ where $R_2$ and $R_3$ are as defined above. The anhydride is conveniently prepared by addition of the olefin or polyolefin across the double bond of maleic anhydride by processes known per se. The invention is illustrated by the following examples.

Preparation of Compounds

A. A reaction mixture containing 59 g of maleic anhydride together with 190 g of a polyisobutylene, such as NAPVIS XD 35 (available from BP), was heated at 230° C. for 16 hours. After this period the solution was vacuum distilled for 4 hours and then cooled to room temperature. 170 g of toluene and 81 g of diethylene glycol were then added and the mixture was heated at 140° C. for 8 hours with reaction product water continuously removed. The reaction mixture was cooled to room temperature and the viscous liquid remaining in the reactor was used directly as fuel additive.

B. 50 g of maleic anhydride was added over 3 hours to 200 g of a polyisobutylene, such as INDOPOL L14 (available from Amoco), which was heated to 200° C. The reaction mixture was then heated at 200° C. for a further 16 hours. After this period the reaction mixture was vacuum distilled for 2 hours and then cooled to room temperature. 186 g of ethylene glycol was then added to the reaction mixture and the mixture was heated at 170° for 12 hours. After this period the reaction mixture was vacuum distilled for 2 hours and then cooled to room temperature. The viscous liquid remaining in the reactor was used directly as fuel additive.

C. A reaction mixture containing 18 g of ethylene glycol together with 35 g of 2-dodecen-1-ylsuccinic anhydride and 36 g of toluene was heated to 160° C. with Dean Stark water removal until the reaction was completed. The viscous liquid remaining in the reactor was used directly as fuel additive.

D. 358 g of polyisobutenylsuccinic anhydride, prepared from maleic anhydride and NAPVIS X10 (available from BP) in the same manner as (B) above, was mixed with 372 g of ethylene glycol and the mixture was heated at 170–190° C. for 12 hours with continuous removal of by-product water. After this period the reaction mixture was vacuum distilled for 2 hours then cooled to room temperature. The viscous liquid can be used directly as a fuel additive or can be diluted with SHELLSOL AB (available from Shell).

Improvement of Fuel Lubricity

A High Frequency Reciprocating Rig (HFRR) bench test, such as described in SAE Technical Paper 932692, can measure the lubricity of base fuels and fuels dosed with lubricity additives. The results of such a test are reported as ball wear in terms of mean wear scar diameter. Lower wear scar diameters are indicative of better lubricity. HFRR wear scar diameter results (in $\mu$) are compared below for typical North European middle distillate fuels which have been treated with compounds of formula (I), a commercial fatty acid based additive, and an alkyl ester of a commercial fatty acid (ethyl linoleate) respectively. The fuels contain less than 0.05% w/w sulphur content.

|  | Base Fuel | 50 ppm | 100 ppm | 200 ppm |
|---|---|---|---|---|
| Commercial Fatty Acid Based Additive | 525 |  | 471 | 434 |
| Ethyl Linoleate | 513 |  | 590 | 578 |
| Compound B | 525 |  | 420 | 380 |
| Compound C | 525 |  | 454 | 426 |
| Compound A | 660 | 555 | 552 |  |

Interaction Tests

Precipitation tests can be employed as an indication of the severity of the interactions between lubricity additive and lubricants, a typical test is described in SAE Technical Paper 872119. Interaction test results are presented below for compound B and a commercial fatty acid additive.

|  | DAY | | | | | | | |
|---|---|---|---|---|---|---|---|---|
|  | 0 | 1 | 2 | 3 | 4 | 5 | 6 | 7 |
| 100 mg/L Commercial Fatty Acid Based Additive | — | — | — | 1 | * | * | 2 | 2 |
| 300 mg/L Commercial Fatty Acid Based Additive | — | — | 1 | 2 | * | * | 3 | 3 |
| 100 mg/L Compound B | — | — | — | — | * | * | — | — |
| 300 mg/L Compound B | — | — | — | — | * | * | — | — |

- No Precipitate
1 Minute Trace
2 Trace Precipitate
3 Light Precipitate
4 Medium Precipitate
5 Heavy Precipitate
$ Sticky Precipitate
* Not Rated (Weekend)

Corrosion Inhibition in Fuels

A standardised corrosion test, such as the National Association of Corrosion Engineers (NACE) standard test TM-01-72, can measure the effectiveness of corrosion inhibitors which are introduced into pipeline cargoes to prevent rusting caused by traces of moisture condensing from the products. The results of such a test are reported as a relative rating on the scale A–E. Corrosion ratings and percentage rust are compared below for samples of iso-octane which has been treated with a compound of formula (I), a commercial fatty acid based additive and a commercial non-acid lubricity additive. Iso-octane is employed for this test as a standard fuel medium to eliminate fuel-dependent effects.

| Conc Additive (mg/l) in iso-octane | 0 | 5.7 | 11.4 | 22.8 |
|---|---|---|---|---|
| Commercial fatty acid based additive | E 90 | A 0 | — | — |
| Compound B | E 90 | B++ 0.5 | A 0 | A 0 |
| Commercial non-acid lubricity additive | E 90 | D 60 | B 15 | B 15 |

| Rating | Proportion of test surface rusted |
|---|---|
| A | None |
| B++ | Less than 0.1% (2 or 3 spots of no more than 1 mm diameter) |
| B+ | Less than 5% |
| B | 5% to 25% |
| C | 25% to 50% |
| D | 50% to 75% |
| E | 75% to 100% |

Maintenance of Corrosion Inhibition in "Custic" Fuels

The reduction in corrosion inhibitor effectiveness in fuels containing alkali is demonstrated by the inhibitor's resistance to caustic extraction. One such caustic extraction screening test involves dosing fuels with 5% v/v of 8% w/w NaOH(aq) and then 5% v/v H$_2$O before corrosion testing via the NACE protocol.

| Conc Additive (mg/l) in iso-octane | 0 | 4.3 | 8.6 |
|---|---|---|---|
| Commercial fatty acid based additive | E 90 | E 90 | E 90 |
| Compound B | E 90 | B+ 2 | B+ 2 |

What is claimed is:

1. A method of increasing the lubricity of a middle distillate fuel, kerosine or heavy fuel oil fuel comprising adding to said fuel of a compound of formula (I)

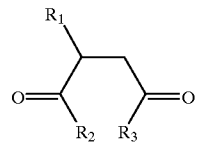

where $R_1$ is a $C_{10}$–$C_{32}$ alkenyl group and $R_2$ and $R_3$ are —(—OCH$_2$CH$_2$—)$_n$OH, —(—OCH$_2$CHCH$_3$—)$_n$OH or —OCH$_2$CHOHCH$_2$OH in which n is 1 or 2.

2. A method of inhibiting corrosion on a metal surface exposed to a middle distillate fuel, kerosine or heavy fuel oil fuel, comprising adding to said fuel of a compound of formula (I)

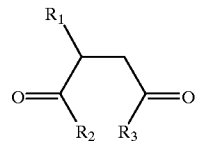

where $R_1$ is a $C_{10}$–$C_{32}$ alkenyl group and $R_2$ and $R_3$ are —(—OCH$_2$CH$_2$—)$_n$OH, —(—OCH$_2$CHCH$_3$—)$_n$OH or —OCH$_2$CHOHCH$_2$OH in which n is 1 or 2.

3. A method according to claim 1 or 2 wherein said compound of formula (I) is present in a concentration of 5 to 5000 ppm by weight.

4. A method according to claim 3 wherein said compound is present in a concentration of 10 to 500 ppm by weight.

5. A method according to claim 4 wherein said compound is present in a concentration of 30 to 300 ppm by weight.

* * * * *